(12) United States Patent
Conroy

(10) Patent No.: US 8,455,464 B2
(45) Date of Patent: Jun. 4, 2013

(54) DEXTRIN CONTAINING COMPOSITIONS FOR PREVENTION OF ADHESIONS

(75) Inventor: Susan Conroy, St. Albans (GB)

(73) Assignee: Innovata Limited (GB)

( * ) Notice: Subject to any disclaimer, the term of this patent is extended or adjusted under 35 U.S.C. 154(b) by 163 days.

(21) Appl. No.: 10/181,658

(22) PCT Filed: Jan. 19, 2001

(86) PCT No.: PCT/GB01/00193
§ 371 (c)(1),
(2), (4) Date: Dec. 9, 2002

(87) PCT Pub. No.: WO01/52866
PCT Pub. Date: Jul. 26, 2001

(65) Prior Publication Data
US 2003/0153529 A1 Aug. 14, 2003

(30) Foreign Application Priority Data

Jan. 21, 2000 (GB) .................................. 0001352.4
Jun. 21, 2000 (GB) .................................. 0015035.9

(51) Int. Cl.
*A61K 31/715* (2006.01)
(52) U.S. Cl.
USPC ............ 514/58; 514/779; 514/885; 424/423; 424/488; 536/103
(58) Field of Classification Search
USPC ......................................... 424/400, 484, 488
See application file for complete search history.

(56) References Cited

U.S. PATENT DOCUMENTS 5,318,780 A * 6/1994 Viegas et al. ................. 424/427
5,891,418 A * 4/1999 Sharma ......................... 424/1.69

FOREIGN PATENT DOCUMENTS

| WO | WO-92/21354 | * 12/1992 |
| WO | WO 99/58168 | * 11/1999 |
| WO | WO-99/58168 | * 11/1999 |
| WO | WO 01/12231 | 2/2001 |

OTHER PUBLICATIONS

Peers, Elizabeth, et al., *Icodextrin Provides Long Dwell Peritoneal Dialysis and Maintenance of Intraperitoneal Volume*, Artificial Organs, vol. 22, No. 1, pp. 8-12 (1998).
Abstract, Conroy, Susan, et al., In Vitro Viral Vector Stability and Fluid Dynamics of an Intraperitoneal Solution for Delivery of Gene Therapy, $91^{st}$ Annual Meeting American Associate of Cancer Research, Proc. Am. Assoc. Cancer Res., vol. 41, #3339, p. 524 (Apr. 1-5, 2000).
Harris et al. "Analysis of the kinetics of peritoneal adhesion formation in the rat and evaluation of potential antiadhesive agents" *Surgery* 117(6):663-669 (2005).
Dobbie, J.W. (1997) "Separation of Peritoneal Surfaces Through the Maintenance of an Artificial Ascites as a Preventative of Peritoneal Adhesions" Abstract, from *The $4^{th}$ Peritoneum and Peritoneal Access Meeting*, Sep. 16-19, 1997.
ML Laboratories, "Adhesions" *PanMureGordon* (Mar. 20, 1998.
Treutner et al. "Prevention of Postoperative Adhesions by Single Intraperitoneal Medication", *Journal of Surgical Research* 59:764-771 (1995).
U.S. Appl. No. 09/700,057.
U.S. Appl. No. 11/257,943.

* cited by examiner

*Primary Examiner* — Humera N. Sheikh
*Assistant Examiner* — Hasan Ahmed
(74) *Attorney, Agent, or Firm* — Myers Bigel Sibley & Sajovec, P.A.

(57) ABSTRACT

A composition for the treatment of adhesions that are formed as a result of an inflammatory response comprising an aqueous formulation containing the polysaccharide dextrin in an effective amount. The invention also discloses a method of treating adhesions that are formed as a result of an inflammatory response.

12 Claims, 3 Drawing Sheets

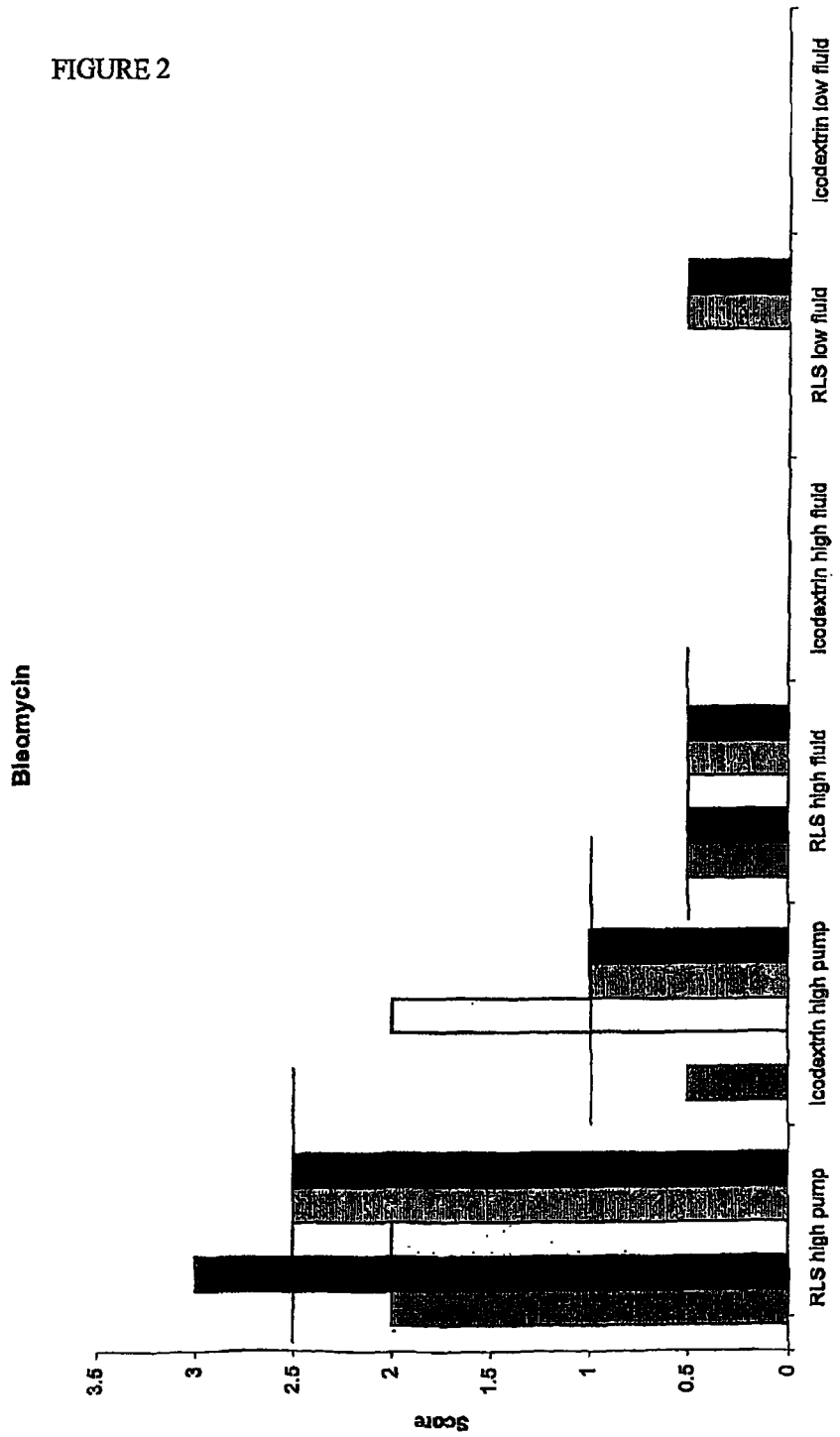

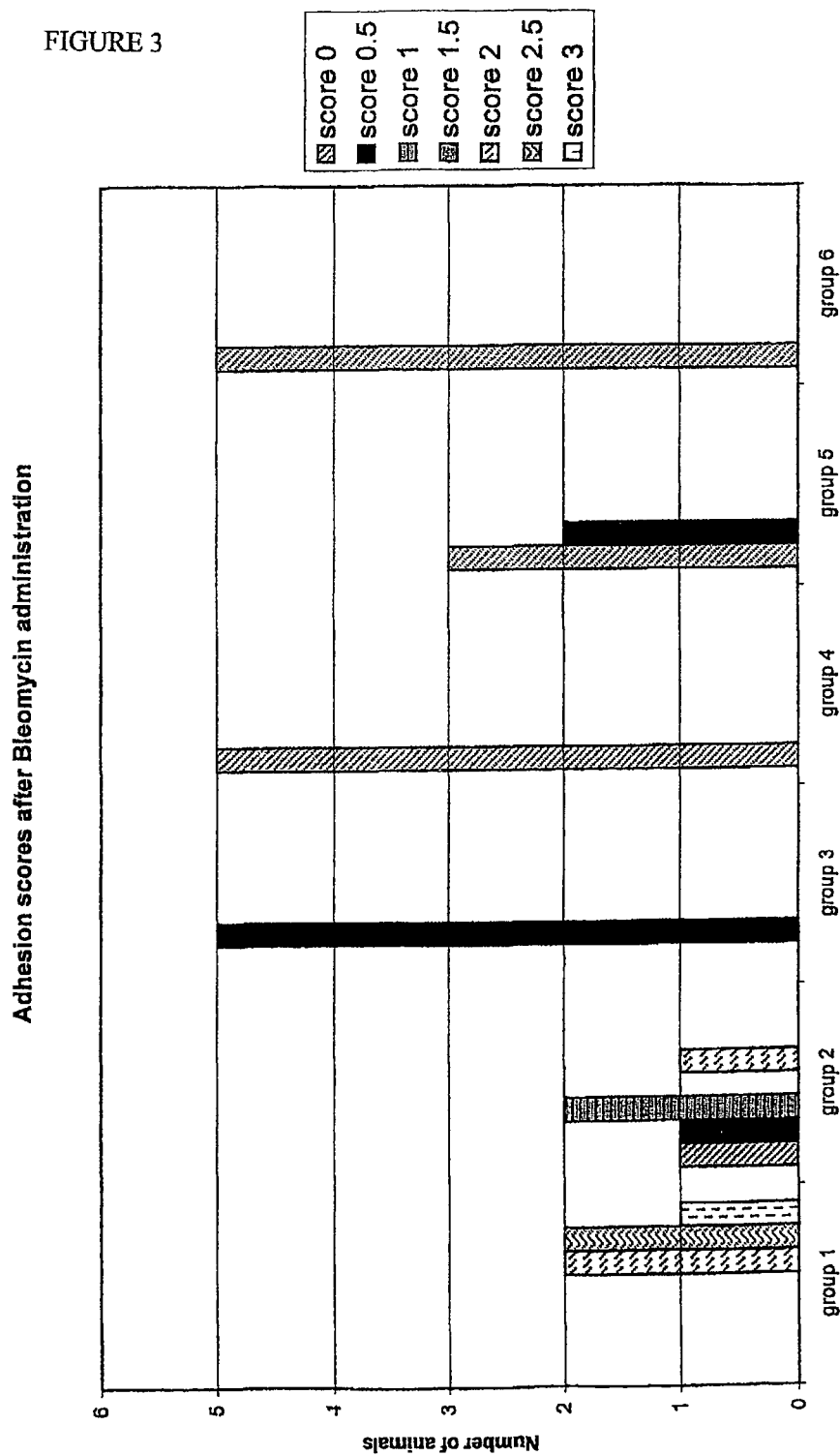

DEXTRIN CONTAINING COMPOSITIONS FOR PREVENTION OF ADHESIONS

RELATED APPLICATIONS

The present application claims priority from International Application No. PCT/GB01/00193, filed on 19 Jan. 2001, which in turn claims priority from Great Britain application No. 0001352.4, filed on 21 Jan. 2000 and Great Britain application No. 0015035.9, filed on 21 Jun. 2000, the disclosures of which are hereby incorporated herein by reference in their entirety.

The present invention relates to the prevention of adhesions, and in particular to adhesions formed in serous cavities such as the peritoneum, the pericardium, the plura and synovial cavities such as joints and tendons, the adhesions being formed as a result of an inflammatory response. Reference will be made hereinbelow to the prevention of adhesions in the peritoneum but it should be understood that the present invention has applicability in connection with other serous cavities in both humans and animals.

BACKGROUND OF THE INVENTION

Adhesions are typically formed in response to mechanical/surgical insult. They are a well documented post-surgical event. It is known to ameliorate the condition by introducing film-forming biocompatible agents into the body cavity around the area of the wound. However, we have found surprisingly that adhesions can also occur in patients suffering from ovarian cancer who receive chemotherapeutic agents via the i.p. route. In other words the adhesions are not formed in response to post-operative events. We believe that it is the chemical insult of the chemotherapeutic agent itself, rather than the possible mechanical injury by i.p administration that induces adhesion formation in these patients. These unexpected observations, we believe, are due to an inflammatory response in these patients to the drugs which they receive. The present invention seeks to provide a composition for use in preventing adhesions that are formed as a result of the inflammatory response.

The treatment of patients with inflammation has two primary objectives, the first being to relieve pain which is typically the presenting problem, and the second is to reduce/halt the tissue-damaging process. Conventional treatment for acute and/or chronic inflammation is to administer non-steroidal anti-inflammatory drugs or glutocorticoids, however administration of these classes of pharmaceutical can cause undesired side effects in some individuals and even dependency.

STATEMENT OF THE INVENTION

According to a first aspect of the present invention there is provided a method of preventing or reducing the incidence of adhesions in or associated with a body cavity, the adhesions being formed as a result of an inflammatory response, other than post-operative adhesions, the method comprising introducing into the body cavity an aqueous solution or suspension or gel formulation containing the polysaccharide dextrin.

Reference herein to an inflammatory response is intended to include chronic inflammatory conditions, such as and without limitation, pelvic inflammatory disease, arthritis, chronic inflammatory bowel disease, ulcerative colitis, Crohn's disease, irritable bowel syndrome and/or acute inflammatory conditions such as those induced by tissue injury the tissue injury being as a result of chemical insult.

The term "dextrin" means a glucose polymer which is produced by the hydrolysis of starch and which consists of glucose units linked together by means mainly of α-1,4 linkages. Typically dextrins are produced by the hydrolysis of starch obtained from various natural products such as wheat, rice, maize and tapioca. In addition to α-1,4 linkages, there may be a proportion of α-1,6 linkages in a particular dextrin, the amount depending on the starch starting material. Since the rate of biodegradability of α-1,6 linkages is typically less than that for α-1,4 linkages, it is preferred that, for many applications, the percentage of α-1,6 linkages is less than 10% and more preferably less than 5%.

Any dextrin is a mixture of polyglucose molecules of different chain lengths. As a result no single number can adequately characterize the molecular weight of such a polymer. Accordingly, various averages are used, the most common being the weight average molecular weight (Mw) and the number average molecular weight (Mn). Mw is particularly sensitive to changes in the high molecular weight content of a polymer whilst Mn is largely influenced by changes in the low molecular weight content of the polymer.

It is preferred that the Mn of the dextrin is in the range of from 1,000 to 30,000 and ideally the Mw is in the range of from 3,000 to 50,000. More preferably, the Mn is from 3,000 to 8,000 and the Mw is from 5,000 to 50,000.

The term "degree of polymerisation" (DP) can also be used in connection with polymer mixtures. For a single polymer molecule, DP means the number of polymer units. For a mixture of molecules of different DP's, weight average DP and number average DP correspond to Mw and Mn. In addition, DP can also be used to characterize a polymer by referring to the polymer mixture having a certain percentage of polymers of DP greater than a particular number or less than a particular number.

It is preferred that the dextrin contains more than 15% of polymers of DP greater than 12 and, more preferably, more than 50% of polymers of DP greater than 12.

The dextrin used in the present invention is water soluble or at least forms a suspension in water or a gel formulation. The dextrin used in this invention may be in the form of either unsubstituted dextrin (as obtained by the hydrolysis of starch) or may be substituted by one or more different groups. The substituents may be negatively charged groups, for instance, sulfate groups, neutral groups, or positively charged groups, for instance, quaternary ammonium groups. In the case where the substituent group is sulfate, it is preferred that the sulfated polysaccharide contains at least one sulfate group per saccharide (glucose) unit.

The present invention also provides a composition comprising an aqueous solution or suspension or gel formulation of the polysaccharide dextrin in which the amount of dextrin is effective to prevent or reduce the incidence of adhesions that are formed as the result of an inflammatory response, other than post-operative adhesions.

The present invention further provides the use of a composition in the prevention or reduction of the incidence of adhesions that are formed as the result of an inflammatory response, other than post-operative adhesions, the composition comprising an aqueous solution or suspension or gel formulation of the polysaccharide dextrin.

The present invention further provides the use of the polysaccharide dextrin in the manufacture of a composition comprising an aqueous solution or suspension or gel formulation of dextrin for preventing or reducing the incidence of adhesions that are formed as the result of an inflammatory response, other than post-operative adhesions, in humans and animals.

Dextrin is a useful material for the production of an adhesion-preventing composition because, inter alia, it is non-toxic, cheap and has the ability to hold fluid in a body cavity. It is also readily metabolised within the body.

Preferably, a composition of the invention is applied to the appropriate body cavity or area before, during or after the inflammatory response.

In the instance of the inflammatory response being as a result of chemical insult by chemotherapy, the composition of the invention may be applied to the body cavity prior to the administration of the chemotherapeutic agent, alternatively it may be applied at the same time or after administration of the chemotherapeutic agent.

Preferably, the composition of the invention is co-administered in the manner as aforedescribed with one or more agent selected from the group consisting of a chemotherapeutic agent, a gene therapy agent, an antibiotic or antiviral agent or any other agent which causes an inflammatory response.

Reference herein to gene therapy agent is intended to include a viral vector the vector being an adenovirus, a retrovirus, a herpesvirus, a plasmid, a phage, a phagemid or a liposome or any other vehicle into which the gene therapy product has been inserted.

Preferably, the composition of the present invention is allowed to remain in the body cavity for a minimum of 2 to 3 days and especially over the period during which the inflammatory response is at a maximum. More preferably, the composition should remain in the body cavity for a period of up to 7 to 8 days.

Preferably, a composition of the invention should be applied to the body cavity in a volume large enough to keep the surfaces apart and/or to dilute chemotactic signals/cells involved in an inflammatory response. For the peritoneum, the volume should preferably be in the range 500-2000 ml and, more preferably, about 1000 ml-1500 ml.

Preferably, the composition should be applied to the appropriate body cavity or area in differing concentrations ideally over a concentration range of 2.5-20% and more ideally over a concentration range of 3-5% and most ideally at about 4% by weight, said concentration range is selected for a specified time span, even more ideally the concentration range is selectively altered over a period of time.

Preferably, the composition should include a concentration of dextrin which is such that the fluid largely holds in place over the period it resides in the cavity. Where a composition includes 4% by weight of dextrin then a suitable dwell period for one infusion might be of the order of 2 to 3 days. A high concentration is liable to cause ingress of fluid. A second infusion at day 3 may extend the total dwell period from 6 to 7 days.

Alternatively, a composition having a dextrin concentration of from 12 to 15% by weight may be used in a smaller volume (perhaps about 750 ml) and will be subject to ingress of fluid. However a single infusion might be sufficient for the full 6 to 7 day period.

It will be appreciated that the concentration of the composition of the invention, the timing of administration and the dwell time are variable and may be selected according to a user's requirements. For example if a chemotherapeutic agent were to be administered over a period of several weeks then the composition of the present invention may be given for the same or extended duration of the therapy and at least until the inflammatory response had abated/ceased. The variations of a dosing regimen are not intended to limit the scope of the application.

Comparing dextrin with dextran, the latter has relatively poor biocompatibility. It is subject to immunological hypersensitivity due to its concentration in lymph nodes and its lack of metabolisability. At best, a dextran solution or suspension will act not so much to separate surfaces and therefore prevent adhesions but simply as a lubricant. Dextrin advantageously serves as an osmotic agent, which can maintain the volume of a solution in the peritoneal cavity. The continued presence of the dextrin solution within the cavity serves to separate tissues which otherwise may adhere to each other in addition to dilution of the inflammatory response.

A composition of the present invention may include any one or more of the following: a suitable lubricant such as a phosphospholipid; a calcium binding agent such as EDTA or sodium citrate; a hyaluronate; a prostacyclin or an analogue thereof, a glycocosolaminoglycan; an antibiotic agent or a material/agent which is associated with preventing an infection or build up of bacteria or foreign bodies or the like.

A composition of the present invention may also include a fibrinolytic agent or an analogue thereof, an anti-inflammatory agent or an analogue thereof, dextrin sulphate and/or methylene blue.

The present invention provides a preferred composition comprising an aqueous solution or suspension or gel formulation of dextrin, one or more phosphospholipids and hyaluronate. Such a composition is not only highly effective in preventing adhesions formed as a result of an inflammatory response, other than post operatively, but also has a good shelf life.

According to a further aspect of the invention there is provided a biocompatible, bioresorbable, and non-toxic adhesion prevention kit, the adhesions being formed as a result of an inflammatory response other than post operative adhesions, for use in humans or animals, the kit comprising an aqueous solution or suspension or gel formulation of dextrin as hereinbefore described, and optionally comprising any one or more of the preferred features as hereinbefore for co-administration with an agent that causes adhesions by inducing an inflammatory response.

BRIEF DESCRIPTION OF THE DRAWINGS

The invention will now be described by way of example only with reference to the following Figures and Tables wherein:

Table 1 shows adhesion scores in adriamycin treatment groups receiving differing concentrations of icodextrin compared to controls; and Table 2 shows the number (%) at each score in adriamycin treatment groups receiving differing concentrations of icodextrin compared to controls.

Figure 1:
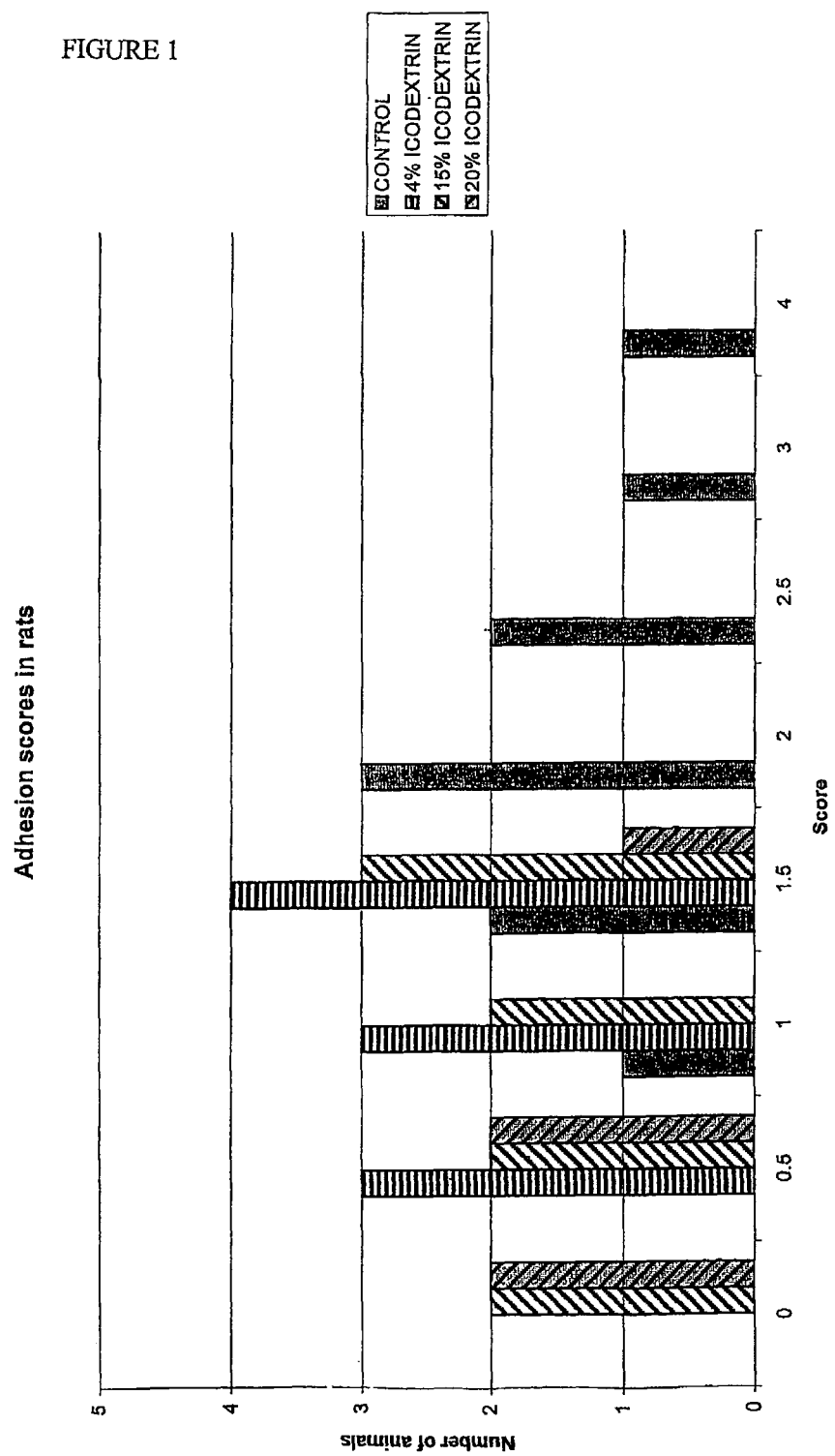

Table 3 shows overall adhesion scores in the treatment group receiving continuous 0.77 U/ml bleomycin in the presence of Ringer's lactated solution (RLS) by pump.

Table 4 shows overall adhesion scores in the treatment group receiving continuous 0.77 U/ml bleomycin in the presence of 4% icodextrin by pump.

Table 5 shows overall adhesion scores in the treatment group receiving 0.77 U/animal bleomycin as a single bolus in 15 ml Ringer's lactated solution (RLS)

Table 6 shows overall adhesion scores in the treatment group receiving 0.77 U/animal bleomycin as a single bolus in 15 ml 4% icodextrin.

Table 7 shows overall adhesion scores in the treatment group receiving 0.077 U/animal bleomycin as a single bolus in 15 ml Ringer's lactated solution (RLS).

Table 8 shows overall adhesion scores in the treatment group receiving 0.077 U/animal bleomycin as a single bolus in 15 ml 4% icodextrin.

FIG. 1 represents a bar chart of number of animals with specific adhesion scores in adriamycin treatment groups receiving differing concentrations of icodextrin compared to controls;

FIG. 2 represents a bar chart of the overall adhesion scores per animal in the six different treatment protocol groups receiving bleomycin.

FIG. 3 represents a bar chart of the adhesion score of each animal in each of the six different treatment protocol groups receiving bleomycin.

DETAILED DESCRIPTION OF THE EMBODIMENTS OF THE INVENTION

We have conducted experiments to evaluate the effect of administration three concentrations (4%, 15% or 20%) of icodextrin in comparison with a control group receiving phosphate buffered saline (PBS) on the formation of adhesions in response to i.p. adriamycin administration in rats. In addition, we provide data on the effect of adhesion formation in rats as a result of administration of bleomycin in conjunction with Ringer's lactated solution (RLS) or 4% icodextrin, either by dosing continuously by pump or as a single bolus dose.

Protocol

Animals:

Female Sprague Dawley rats, 175 to 200 grams, were purchased from and quarantined in the USC Vivaria for at least 2 days prior to use. The animals were housed on a 12:12 light:dark cycle with food and water available ad libitum. Thirty animals were used for the adriamycin experiments and forty for the bleomycin experiments.

Materials:

The 4% [wt/vol], 15% or 20% icodextrin were supplied by ML Laboratories PLC. The sutures used to close the muscle and skin were 4-0 Ethilon (Ethicon, Somerville, N.J.). The sutures to secure the tubing and pump were 5-0 Ethilon. Alzet miniosmotic pumps (10 μl/hour, 2 ml, Model 2M1) were purchased from Alza Corporation (San Francisco, Calif.). Polyethylene tubing was purchased from Clay Adams (VWR, Irvine Calif.).

Surgical Procedure:

Animals were anesthetized with a mixture of 85 mg/kg ketamine hydrochloride and 5 mg/kg Rompum intramuscularly. Following preparation for sterile surgery, a small incision was made at the midline. In animals in which a pump was placed, a polyethylene catheter (Clay Adams polyethylene tubing PE-60 ID 0.76 mm (0.030") OD 1.22 mm (0.048")) was introduced into the peritoneal cavity and sutured to the sidewall with 5-0 Ethilon. The pump was filled with 23.2 μg/ml Adriamycin (10 μl/hour over in life phase) or with 0.77 U/ml bleomycin (0.0077 U/hour) and placed in the subcutaneous space. The catheter was then attached to the pump and the midline muscle incision was closed around the catheter. Prior to closure of the last stitch, a 21-gauge catheter was introduced into the peritoneal cavity and a purse string suture was placed through the muscle around the catheter. In the adriamycin experiments, 20 ml of solution (4%, 15% or 20% icodextrin or PBS) were administered. In the bleomycin experiments 15 ml of RLS or 4% icodextrin were administered to the treatment groups as stated below. Subsequently, the skin incision was then closed with 4-0 Ethilon sutures.

| Group | Bleomycin conc. | Mode of Administration | Co-administered compound |
|---|---|---|---|
| 1 | 0.77 U/ml | Pump | RLS |
| 2 | 0.77 U/ml | Pump | Icodextrin |
| 3 | 0.77 U/ml | Fluid (bolus) | RLS |
| 4 | 0.77 U/ml | Fluid (bolus) | Icodextrin |
| 5 | 0.077 U/ml | Fluid (bolus) | RLS |
| 6 | 0.077 U/ml | Fluid (bolus) | Icodextrin |

Seven days after the initiation of adriamycin treatment and nine days after bleomycin treatment, the rats were euthanized by $CO_2$ and the extent of adhesion formation was evaluated. Adhesions were expected in the areas around the catheter, between the catheter and intestines or liver and between the lobes of the liver. The overall score was based upon the extent of adhesion formation and the number of sites involved in adhesion formation. This was a qualitative assessment based upon the appearance of the abdomen. The scoring system used to report adhesions in these studies is as follows:

0 No adhesions found in the peritoneal cavity 0.5+ Only a few, very filmy adhesions between the sidewall and catheter. Essentially no or very little fibrin-like substance covering the catheter 1.0+ Adhesions present between the sidewall and catheter with mild bowel or liver adhesions (to itself not catheter). Mild fibrin-like covering around catheter.

1.5+ Adhesions involving the liver and/or bowel and catheter. The covering on the catheter is more extensive than 1.0+.

2.0+ Adhesions as with 1.5+ with increase fibrin covering on the catheter and increased density of liver and/or bowel adhesions to catheter.

2.5+ Adhesions as described in 2.0+ but are more dense.

3.0+ More sites are involved in adhesions than in animals scored with 2.5+

4.0+ Sites (catheter to sidewall, liver, bowel and organs to themselves) as in 3.0+, but more than one site involves dense, nondissectable adhesions.

The animals were evaluated by two independent, blinded observers. If there was a disagreement as to the score, the higher one was given. Overall adhesion scores were given that took into account all of the adhesion and fibrosis scores listed above.

Statistical Methods

Non-parametric statistics were used to analyze the adriamycin data as there were 10 rats per treatment group and results were ordinal data from a scoring system.

The overall treatment effect was tested using the Kruskal-Wallis test. Further investigations in the presence of a treatment effect were to investigate each icodextrin concentration compared to the control group, using the Wilcoxon rank sum statistic.

Adriamycin Results

Ten animals pre treatment group were studied. In the control group and the 4% icodextrin group all animals were assessed for adhesion formation. In the 15% icodextrin group 1 rat was not assessed. Five (50%) of the rats in the 20% icodextrin group were euthanized early due to abdominal bulging and were not scored. The number of animals (%) at each score is presented in Table 2.

There was an overall treatment effect (p<0.001), using the Kruskal-Wallis test. Using the Wilcoxon rank sum statistic differences between each icodextrin group and the control group were investigated. There were significant differences between the 4% icodextrin group (p<0.01), the 15% icodextrin group (p<0.01), 20% icodextrin group (p<0.05) and the control group. Adhesion scores were lower in all the icodextrin groups than in the control groups (FIG. 1). All adhesion scores in the icodextrin groups were 1.5 or less (Table 1).

From our studies we have shown that all three icodextrin groups had significantly lower adhesion scores than the crystalloid solution and that administration of icodextrin at the end of the procedure reduced the formation of adhesions formed as a result of chemotherapy. The efficacy of the reduction of adhesion formation increased as the percentage of icodextrin was increased. However in the group of animals that received 20% icodextrin, half of the animals were euthanized early due to abdominal bulging and were not scored.

Bleomycin Results

Continuous administration of bleomycin resulted in substantial adhesions in the presence of Ringer's lactated solution (RLS), Table 3 Group 1, Rank 7.8±0.9. In the presence of icodextrin, this was significantly reduced (Table 4, Rank 3.2±1.0, p=0.02). Administration of bleomycin in a single bolus resulted in less fibrosis (Table 5, Rank 8.0±0.0 and Table 7, Rank 6.5±1.4). However, at the higher concentration of bleomycin, administration of the chemotherapeutic in the presence of icodextrin significantly reduced adhesion formation (Table 6, Rank 3.0±0.0, p=0.004 and Table 8, Rank 4.5±0.0, p=0.18). The p values given are for comparison of the ranks of the most comparable RLS and icodextrin-treated groups using the Wilcoxon signed rank test. The results are tabulated below:

| Bleomycin Conc | Dose Regimen | Rank Score RLS | Rank Score 4% icodextrin | P value |
|---|---|---|---|---|
| 0.77 U/ml | pump | 7.8 ± 0.9 | 3.2 ± 1.0 | P = 0.02 |
| 0.77 U/ml | bolus | 8.0 ± 0.9 | 3.0 ± 0.0 | P = 0.004 |
| 0.077 U/ml | bolus | 6.5 ± 1.4 | 4.5 ± 0.0 | P = 0.18 |

In summary, the adhesiogenic effect of a high dose of bleomycin (0.77 U/ml) administered either continuously by pump in either RLS or 4% icodextrin (Groups 1 and 2) or as a single bolus dose (Groups 3 and 4) were compared. In addition a comparison between high dose (Groups 3 and 4) and a ten fold lower dose of bleomycin (0.077 U/ml; Groups 5 and 6) as a single bolus doses were compared. Our results have shown that 4% icodextrin is significantly more effective than RLS at preventing adhesion formations as a result of dosing with 0.77 U/ml bleomycin, irrespective of the dosing regimen being continuous or by a single bolus. No differences between 4% icodextrin and RLS was observed at the lower dose of bleomycin (0.077 U/ml) as virtually no adhesions were formed by this concentration of bleomycin.

The dextrin composition of the present invention is therefore useful as preventing adhesion that occur as a result of chemotherapeutic injury and inflammatory responses.

TABLE 1

Adhesion Scores in Rats Receiving 20 ml Phoshate Buffered Saline Solution (PBS) or icodextrin

| PBS | 4% icodextrin | 15% icodextrin | 20% icodextrin |
|---|---|---|---|
| 1 | 0.5 | 0 | 0 |
| 1.5 | 0.5 | 0 | 0 |
| 1.5 | 0.5 | 0.5 | 0.5 |
| 2 | 1 | 0.5 | 0.5 |
| 2 | 1 | 1 | 1.5 |
| 2 | 1 | 1 | |
| 2.5 | 1.5 | 1.5 | |
| 2.5 | 1.5 | 1.5 | |
| 3 | 1.5 | 1.5 | |
| 4 | 1.5 | | |

TABLE 2

Number (%) at each score

| Score | Control | 4% icodextrin | 15% icodextrin | 20% icodextrin |
|---|---|---|---|---|
| 0 | 0 | 0 | 2 (22%) | 2 (40%) |
| 0.5 | 0 | 3 (30%) | 2 (22%) | 2 (40%) |
| 1 | 1 (10%) | 3 (30%) | 2 (22%) | 0 |
| 1.5 | 2 (20%) | 4 (40%) | 3 (33%) | 1 (20%) |
| 2 | 3 (30%) | 0 | 0 | 0 |
| 2.5 | 2 (20%) | 0 | 0 | 0 |
| 3 | 1 (10%) | 0 | 0 | 0 |
| 4 | 1 (10%) | 0 | 0 | 0 |

TABLE 3

Group 1: Bleomycin 0.77 U/ml in RLS with pump

| Catheter | Liver | Sidewall | Bowel | Liver-Catheter | Bowel-Catheter | Capsulation | Omentum | Horn-Catheter | Score |
|---|---|---|---|---|---|---|---|---|---|
| 3 | 1 | — | — | — | — | 2 | — | 2 | 2 |
| 3 | — | — | 1 | — | — | 2 | — | 3 | 3 |
| 2 | — | — | — | — | 1 | 1 | — | 2 | 2.0 |
| 2 | 2 | — | — | — | 3 | — | — | — | 2.5 |
| 3 | 2 | — | — | — | — | 2 | — | 2 | 2.5 |

TABLE 4

Group 2: Bleomycin 0.77 U/ml in 4% icodextrin with pump

| Catheter | Liver | Sidewall | Bowel | Liver-Catheter | Bowel-Catheter | Capsulation | Omentum | Horn-Catheter | Score |
|---|---|---|---|---|---|---|---|---|---|
| 2 | — | — | — | — | — | — | — | — | 0.5 |
| — | — | — | — | — | — | — | — | — | 0 |
| 3 | — | — | — | — | — | — | — | 2 | 1 | 2.0 |

TABLE 4-continued

Group 2: Bleomycin 0.77 U/ml in 4% icodextrin with pump

| Catheter | Liver | Sidewall | Bowel | Liver-Catheter | Bowel-Catheter | Capsulation | Omentum | Horn-Catheter | Score |
|---|---|---|---|---|---|---|---|---|---|
| 2 | — | — | — | — | — | — | — | — | 1 |
| 1 | — | — | — | — | — | 1 | 1** | — | 1 |

TABLE 5

Group 3: Bleomycin 0.77 U/rat in RLS 15 ml IP

| Catheter | Liver | Sidewall | Bowel | Liver-Catheter | Bowel-Catheter | Capsulation | Omentum | Horn-Catheter | Score |
|---|---|---|---|---|---|---|---|---|---|
| — | 1* | 1 | — | — | — | — | — | — | 0.5 |
| — | 1* | — | 1 | — | — | — | 1** | — | 0.5 |
| — | 1* | — | — | — | — | — | — | — | 0.5 |
| — | 1* | — | — | — | — | — | 1** | — | 0.5 |
| — | 1* | — | — | — | — | — | 1** | — | 0.5 |

TABLE 6

Group 4: Bicomycin 0.77 U/rat in 4% icodextrin 15 ml IP

| Catheter | Liver | Sidewall | Bowel | Liver-Catheter | Bowel-Catheter | Capsulation | Omentum | Horn-Catheter | Score |
|---|---|---|---|---|---|---|---|---|---|
| — | — | — | 1** | — | — | — | — | — | 0 |
| — | — | — | 1** | — | — | — | — | — | 0 |
| — | — | — | — | — | — | — | — | — | 0 |
| — | 1* | — | — | — | — | — | — | — | 0 |
| — | — | — | 1(SI+)** | — | — | — | — | — | 0 |

+SI refers to the involvement of the small intestine.

TABLE 7

Group 5 Bleomycin 0.077 U/rat in RLS 15 ml IP

| Catheter | Liver | Sidewall | Bowel | Liver-Catheter | Bowel-Catheter | Capsulation | Omentum | Horn-Catheter | Score |
|---|---|---|---|---|---|---|---|---|---|
| — | — | — | — | — | — | — | 1** | — | 0 |
| — | — | — | — | — | — | — | — | — | 0 |
| — | — | — | 1** | — | — | — | 1** | — | 0 |
| — | — | — | 1 | — | — | — | — | — | 0.5 |
| — | — | — | 1 | — | — | — | — | — | 0.5 |

TABLE 8

Group 6: Bleomycin 0.077 U/rat in 4% icodextrin 15 ml IP

| Catheter | Liver | Sidewall | Bowel | Liver-Catheter | Bowel-Catheter | Capsulation | Omentum | Horn-Catheter | Score |
|---|---|---|---|---|---|---|---|---|---|
| — | 1 | — | — | — | — | — | — | — | 0 |
| — | — | — | — | — | — | — | — | — | 0 |
| — | — | — | — | — | — | — | — | — | 0 |
| — | — | — | — | — | — | — | — | — | 0 |
| — | — | — | — | — | — | — | — | — | 0 |

*refers to fibrosis not adhesion
**refers to inflammation not adhesion

The invention claimed is:

1. A method of reducing the incidence of non-post operative adhesions in or associated with a peritoneal cavity, the adhesions being formed as a result of an inflammatory response in the peritoneal cavity to an inflammatory response causative agent, the method comprising:
   (a) causing an inflammatory response in the peritoneal cavity as a result of a chemical insult or administration of an agent that can cause an inflammatory response; and
   (b) administering an aqueous formulation containing the polysaccharide dextrin into the peritoneal cavity,
wherein the aqueous formulation is administered simultaneously with the inflammatory response causative agent and wherein the inflammatory response causative agent is selected from the group consisting of a chemotherapeutic agent, a gene therapy agent, an antibiotic agent and an antiviral agent and wherein the composition is allowed to remain in the peritoneal cavity for a minimum of 2 to 3 days.

2. A method according to claim 1 wherein the aqueous formulation is a solution.

3. A method according to claim 1 wherein said formulation is applied to the peritoneal cavity at the same time as administering a chemotherapeutic or gene therapy agent.

4. A method according to claim 1 wherein the composition is allowed to remain in the peritoneal cavity over the period of the inflammatory response.

5. A method according to claim 1 wherein the composition remains in the peritoneal cavity for a period of up to 7 to 8 days in order to allow restoration of non-stick surfaces (mesothelium regeneration).

6. A method according to claim 1 wherein the composition is applied to the peritoneal cavity in a volume large enough to keep tissue surfaces apart.

7. A method according to claim 1 wherein the volume of the composition applied to the peritoneal cavity is in the range 500-2000 ml.

8. A method according to claim 7 wherein the volume of the composition applied to the peritoneal cavity is in the range 1000 ml-1500 ml.

9. A method according to claim 1 wherein the dextrin is applied to the peritoneal cavity in differing concentrations over a concentration range of 2.5-18% by weight.

10. A method according to claim 9 wherein the dextrin is applied to the peritoneal cavity in differing concentrations over a concentration range of 3-5% by weight.

11. A method according to claim 9 wherein the dextrin is applied to the peritoneal cavity in an amount of about 4% by weight.

12. A method of reducing the incidence of adhesions in a peritoneal cavity formed as a result of an inflammatory response, the method comprising administering simultaneously the following to the peritoneal cavity:
   (a) an aqueous formulation comprising a polysaccharide dextrin in an amount effective to reduce said adhesions, wherein the dextrin has more than 15% of polymers with a degree of polymerization (DP) greater than 12, and
   (b) an inflammatory response causative agent selected from the group consisting of a chemotherapeutic agent and an antibiotic agent, wherein the composition is allowed to remain in the peritoneal cavity for a minimum of 2 to 3 days, and administration of the polysaccharide dextrin reduces the incidence of adhesions formed in the peritoneal cavity as a result of an inflammatory response caused by the inflammatory response causative agent.

* * * * *

UNITED STATES PATENT AND TRADEMARK OFFICE
CERTIFICATE OF CORRECTION

| | | |
|---|---|---|
| PATENT NO. | : 8,455,464 B2 | Page 1 of 1 |
| APPLICATION NO. | : 10/181658 | |
| DATED | : June 4, 2013 | |
| INVENTOR(S) | : Conroy | |

It is certified that error appears in the above-identified patent and that said Letters Patent is hereby corrected as shown below:

<u>In the Claims</u>:
Column 12, Claim 12, Line 29:
    Please correct "of 2 to 3 days, and administration of"
        to read -- of 2 to 3 days, and wherein administration of --

Signed and Sealed this
First Day of July, 2014

Michelle K. Lee
*Deputy Director of the United States Patent and Trademark Office*